United States Patent [19]

Lyttle et al.

[11] Patent Number: 5,717,085
[45] Date of Patent: Feb. 10, 1998

[54] PROCESS FOR PREPARING CODON AMIDITES

[75] Inventors: Matthew H. Lyttle, Point Reyes Station; Lawrence M. Kauvar, San Francisco, both of Calif.

[73] Assignee: Terrapin Technologies, Inc., San Francisco, Calif.

[21] Appl. No.: 344,820

[22] Filed: Nov. 23, 1994

[51] Int. Cl.$^6$ .............................. C07H 1/02; C07H 21/04
[52] U.S. Cl. ................................... 536/25.34; 536/25.3
[58] Field of Search ............................. 536/25.3, 25.6, 536/25.34

[56] References Cited

U.S. PATENT DOCUMENTS 4,415,732  11/1983  Caruthers et al. ............ 536/25.3
5,264,563  11/1993  Huse ............................. 536/25.3

FOREIGN PATENT DOCUMENTS

WO 92/03461  3/1992  WIPO.
WO 93/21203  10/1993  WIPO.

OTHER PUBLICATIONS

Lyttle et al., "Mutagenesis Using trinucleotide β–Cyanoethyl Phosphoramidites", *Biotechniques* 19:274–281 (1995).

Virenkäs et al., "Trinucleotide phosphoramidites: ideal reagents for the synthesis of mixed oligonucleotides for random mutagenesis" *Nucleic Acids Research*, 22:5600–5607 (1994).

Wakabayashi et al., "Rapid Synthesis of Oligodeoxynucleotides by Using N-Methylimidazole as a Condensation Catalyst. Syntheses of Dodecanucleotides Corresponding to Complementary Deoxyribonucleic Acid of the Tetrapeptide Fragments of Cholecystokinin–Pancreozymin and Vasoactive Intestinal Peptide", *Chem. Pharm. Bull.*, 30:11, 3951–58 (1982).

Ohtsuka et al., "Deoxyribonucleic Acids and Related Compounds. VIII. Solid–Phase Synthesis of Deoxyribooligonucleotides with 3'–Modification by Elongation in the 3'–Direction", *Chem. Pharm. Bull.*, 32:1, 85–93 (1984).

Kumar et al., "Improvements in Oligodeoxyribonucleotide Synthesis: Methyl N,N–Dialkylphosphoramidite Dimer Units for Solid Support Phosphite Methodology", *J. Org. Chem.*, 49:25, 4905–4911 (1984).

Glaser et al., "Antibody Engineering by Codon–based Mutagenesis in a Filamentous Phase Vector System", *J. Immun.*, 149:12, 3903–3913 (1992).

Sondek et al., "A General Strategy for Random Insertion and Substitution Mutagenesis: Substoichiometric Coupling of Trinucleotie Phasphoramidites", *Proc. Natl. Acad. Sci. USA*, 89:3581–85 (1992).

Virnekas et al., "Trinucleotide Phosphoramidites: Ideal Reagents for the Synthesis of Mixed Oligonucleotides for Random Mutagenesis", *Nucleic Acids Research*, 22:25, 5600–5607 (1994).

*Primary Examiner*—Gary L. Kunz
*Attorney, Agent, or Firm*—Morrison & Foerster LLP

[57] ABSTRACT

A process for preparing a trinucleotide phosphoramidite comprising reacting a 3',5'-dihydroxy dinucleoside with a nucleoside 5'-phosphoramidite; oxidizing this trinucleotide phosphite to produce the 3'-hydroxyl trinucleotide; and finally converting the 3'-hydroxy trinucleotide to the 3'-phosphoramidite derivative. Such trinucleotide phosphoramidites provide a convenient route for synthesizing oligonucleotides with randomized codons at specified positions.

6 Claims, 2 Drawing Sheets

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

ATACTTARCA TGAGCC    16

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

ATACTTATCA TGAGCC    16

( 2 ) INFORMATION FOR SEQ ID NO:3:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

CATGCCATGA CTCGCGGCCC AGCCGCCCAT GGCATGCCTC CATACACAGT TGTTTA    56

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_difference
        ( B ) LOCATION: replace(19, "")
        ( D ) OTHER INFORMATION: /note= "This position is (XXX)5."

( x i ) SEQUENCE DESCRIPTION: SEQ ID NO:4:

CCAGCATTCT GCGGCCGCNG GGGAGGTTCA CGTACTCAGG    40

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

CTATGCGGCC CCATTCA    17

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

ATCATGATGA TCCTT    15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

ATGATCATCA TGCTT    15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

AGCAGCATCC TTATC                                                                                   15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

ATCATGATCA TCATC                                                                                   15

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

AGCCTTATCA TC                                                                                      12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

ATCATCATCC TT                                                                                      12

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

ATCCTTATCA TC                                                                                      12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

ATGCTTATCC TT                                                                                      12

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

AGCATCATCC TT                                                                                      12

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:15:

CTTCTTATCA GC                                         12

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:16:

AGCATCATCA TGCTT                                     15

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:17:

ATGATCCTTA TC                                         12

( 2 ) INFORMATION FOR SEQ ID NO:18:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:18:

ATCCTTATCC TT                                         12

( 2 ) INFORMATION FOR SEQ ID NO:19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:19:

AGCATCCTTC TTATC                                     15

( 2 ) INFORMATION FOR SEQ ID NO:20:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:20:

ATCATAATCA TC                                         12

```
( 2 ) INFORMATION FOR SEQ ID NO:21:

( i ) SEQUENCE CHARACTERISTICS:
         ( A ) LENGTH: 12 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:21:

ATCATCAGCA TG                                                              1 2
```

PROCESS FOR PREPARING CODON AMIDITES

TECHNICAL FIELD

The invention relates to the synthesis of various types of oligonucleotides that are useful in analysis, therapy and other applications. More specifically, the invention concerns a technique for using preassembled 3'-phosphoramidite trinucleotides as building blocks to make oligonucleotides encoding a desired sequence of amino acids, optionally containing positions with random amino acids. Randomized DNA fragments, in particular, are useful in producing combinatorial libraries of peptides or proteins with a variety of binding properties, from which molecules of special interest can be selected.

In one popular format, a DNA fragment is synthesized corresponding to the sequence of a bacteriophage coat protein with an appended "scrambled region" where all possible codons will be presented. This fragment family is then inserted into phage DNA such that, in an appropriate host cell population, a library of different expressed peptide regions is created. Selection of phage with desirable characteristics can then be accomplished by a variety of criteria, and the sequence responsible can be determined by sequencing the appropriate portion of the phage DNA.

BACKGROUND ART

Use of molecular biology techniques to encode randomized sets of short peptides, of interest for their own sake or as a means to modify specific sites within protein domains, are useful to select molecules with desirable binding specificities. Trinucleotides carrying certain protecting groups have long been used as intermediates to synthesize oligonucleotides corresponding to specific peptides of interest. For example, see Wakabayashi et al., "Rapid Synthesis of Oligodeoxynucleotides by using N-Methylimidazole as a Condensation Catalyst. Syntheses of Dodecanucleotides Corresponding to Complementary Deoxyribonucleic Acid of the Tetrapeptide Fragments of Cholecystokinin-Pancreozymin and Vasoactive Intestinal Peptide", *Chem. Pharm. Bull.*, 30, 3951–58 (1982).

Certain dodecanucleotides have been synthesized on a solid polymer support with phosphate triester methods by elongation in the 3'-direction. The elongation can occur by condensing the 3'-phosphodiester with 5'-deblocked dinucleotides or trinucleotides having the 3'-(o-chlorophenyl)phosphoro-p-anisidate moiety by using 1-(mesitylene sulfonyl)-3-nitro-1H-1,2,4-tetrazole as the activating reagent. Ohtsuka et al., "Deoxyribonucleic Acids and Related Compounds. VIII. Solid-Phase Synthesis of Deoxyribooligonucleotides with 3'-Modification by Elongation in the 3'-Direction", *Chem. Pharm. Bull.*, 32, 85–93 (1984).

When adapted to solid phase synthesis, the phosphate triester method produces acceptable results for short fragments (10–20 bases in length), but not for the longer fragments needed to incorporate a scrambled sequence into a form suitable for insertion into a vector. Triester methods have largely been replaced by the phosphoramidite technique, which provides better performance in the synthesis of long fragments. For example, methods to increase the yield of long sequences prepared by solid phase synthesis have been reported using 3'-phosphoramidite functionalized, protected nucleotide dimers. Kumar et al., "Improvements in Oligodeoxyribonucleotide Synthesis: Methyl N,N-Dialkylphosphoramidite Dimer Units for Solid Support Phosphite Methodology", *J. Org. Chem.*, 49:25, 4905–4911 (1984).

Due to degeneracy in the DNA code, however, total scrambling of all four nucleotides (adenine, guanine, cytosine and thymine) at each site in a DNA sequence leads to more DNA species than peptide species, with the excess growing geometrically as a function of the length of the scrambled sequence. For a hexapeptide, the 64 million possible combinations of 20 amino acids expands to about 68 billion possible combinations of encoding oligonucleotides. Further, the inadvertent inclusion of stop codons sometimes results in the formation of truncated peptide sequences, which further complicates the analysis.

Two major approaches have been described to overcome this redundancy problem. In a first approach, a semi-scrambled set of nucleotides is used to take advantage of the third-position redundancy in many codon assignments, for example, N-N-(G/C), which symbolizes a trinucleotide having in the first and second positions a random mix of all four nucleosides and, in the third position, a mix of only guanine and cytosine. This reduces the number of triplets from 64 to 32, while still encoding all 20 amino acids, and has only one stop codon.

However, each of the four nucleotides has a different rate of incorporation onto the tip of the growing oligonucleotide chain, so that the yield of the resulting triplets can vary as much as five-fold. Accordingly, to obtain a library containing all hexapeptides, the number of clones that must be examined is more than 15,000 times larger than the number indicated by simple combinatorial arithmetic.

In the second approach, individual codons are sequentially added to an oligonucleotide on a solid support, usually resin beads, which have been divided into separate containers. The contents of the containers are combined before proceeding to the next codon, for which the resin beads holding the growing chains are again separated into individual containers. This resin splitting approach does, in principle, produce a more nearly ideal final library, but requires a great deal of synthetic effort. Huse, U.S. Pat. No. 5,274,563 issued 23 Nov. 1993; and Glaser et al., "Antibody Engineering by Codon-based Mutagenesis in a Filamentous Phage Vector System", *J. of Immun.*, 149:12, 3903–13 (1992). Specifically, handling problems, such as static electricity, make quantitative physical transfer of the beads difficult, and chemical inhomogeneity in the microscopically settled beads can lead to poor coupling on some of the beads during solid phase synthesis.

Further, to obtain reasonably uniform representation of each peptide in a hexapeptide library with this approach, more than 64 million beads must be used to assure that the random pathway taken by each bead through the different containers does not leave out some sequence by mathematical chance. A 1 μM synthesis on controlled pore glass (CPG) beads is typical for synthesis of DNA used in most molecular biology purposes. At this synthesis scale, however, only about 25,000 beads are present, which is too few to represent the entire library. Moreover, even if scale-up is attempted, it is a difficult procedure due to increasingly prohibitive handling problems and the attendant costs.

The Huse patent also speculates in passing that oligonucleotides could be synthesized from nucleotide triplets, but quickly discourages the use of this approach, stating that "the cost of synthesis from such triplets far exceeds that of synthesis from individual monomers because triplets are not commercially available." (See, Huse, column 2, lines 18–29) Unexpectedly, the materials and methods of the invention provide a less labor-intensive procedure than that used in the art and, at the same time, provides increased confidence that all the desired sequences will be available, even on a modest synthetic scale.

DISCLOSURE OF THE INVENTION

According to the present invention, there have been prepared compounds of the formula:

wherein:

W, X, Y and Z are each independently hydrogen or a protecting group;

$B^1$, $B^2$ and $B^3$ are each independently a base selected from the group consisting of protected adenine, protected guanine, protected cytosine, protected or unprotected thymine and protected or unprotected uracil; and A is hydrogen or hydroxy.

Further, a method has been found for making these compounds, comprising the steps of:

a. treating a nucleoside comprising a base, a ribose or deoxyribose residue, and a 5'-protecting group, with a trialkylsilyl halide to produce the corresponding 3'- and 5'-protected nucleoside;

b. removing the 5'-protecting group to produce a 5'-deprotected nucleoside;

c. coupling the 5'-deprotected nucleoside with a first nucleoside phosphoramidite and then oxidizing to form a phosphate triester;

d. deprotecting at the 5'- and 3'-termini to give the corresponding 3',5'-dihydroxy dinucleoside;

e. coupling the dihydroxy dinucleoside with a second nucleoside phosphoramidite and oxidizing to produce the corresponding 3'-hydroxy trinucleotide; and f. converting the 3'-hydroxy trinucleotide to a 3'-phosphoramidite.

In another embodiment, a panel is made up of from two to twenty of these 3'- or 5'-phosphoramidite trinucleotide codons or their complements, where each codon encodes a different amino acid.

Three processes for synthesizing an oligonucleotide are disclosed. To synthesize an oligonucleotide encoding a sequence of "n" pre-determined amino acids, or its complement, the process of the invention comprises the steps of:

(a) coupling a first 3'-phosphoramidite trinucleotide codon, phosphoramidite monomer, or the complement to this codon or monomer, onto a nucleoside- or a nucleotide-bearing solid support;

(b) sequentially condensing with an immediately preceding codon "n" 3'-phosphoramidite trinucleotide codons or their complements, each codon or its complement corresponding to the next pre-determined amino acid in the sequence; and (c) cleaving the oligonucleotide from the solid support.

The automated solid phase supported chemistry used in the invention can include a large number of materials generally known to those of ordinary skill in the art. Examples of such useful materials includes nucleoside-functionalized CPG, i.e., functionalized with deoxyribose cytosine (dC) or another nucleoside, e.g., dG, dU or rC; tetrazole activator solution; acetylating capping solutions; iodine oxidation solutions; dichloroacetic acid deprotecting solvent; and automated DNA synthesizers.

To synthesize an oligonucleotide encoding a peptide having at least one pre-determined amino acid position and at least one random amino acid position, a second synthetic process of the invention comprises the steps of:

(a) coupling a first 3'-phosphoramidite trinucleotide codon, phosphoramidite monomer, or the complement to this codon or monomer, onto a nucleoside or nucleotide monomer-bearing solid support;

(b) for each pre-determined amino acid position, sequentially coupling to an immediately preceding codon a 3'-phosphoramidite trinucleotide codon, or its complement, corresponding to the pre-determined amino acid;

(c) for each random amino acid position, coupling to an immediately preceding codon a mixture of from two to twenty 3'-phosphoramidite trinucleotide codons, at least two of the trinucleotides representing a codon to a different amino acid; and (d) cleaving said nucleotide from the solid support.

Steps (b) and (c) of this process are combined in such a way that each predetermined codon sequentially corresponds to each pre-determined amino acid position in the oligonucleotide.

Further, the identity and ratio of codons used in each such mixture can be made to represent the desired degree of diversity in the corresponding random amino acid position. Thus, if reduced coupling efficiency occurs with particular codons making up the desired oligonucleotide, this defect can be readily overcome by minor adjustments in the relative concentrations of individual codons. For example, dC-functionalized CPG or rC supports may be prone to give unequal incorporation of bases when mixtures are used, perhaps due to steric hindrance. With the invention, this inequality can be compensated for by varying the relative concentrations of the various codons.

To synthesize an oligonucleotide having at least one region of random amino acid positions, the third synthetic process of the invention comprises the steps of:

(a) coupling at least one pre-existing 3'-phosphoramidite trinucleotide codon, phosphoramidite monomer, or the complement to said codon or monomer, onto a nucleoside- or nucleotide-bearing solid support;

(b) for each random amino acid position, sequentially coupling to the immediately preceding codon a mixture of from two to twenty pre-existing 3'-phosphoramidite trinucleotide codons, each codon corresponding to a different amino acid; and (c) cleaving the oligonucleotide from the solid support.

In this process, the identity and ratio of codons used in each such mixture are each representative of the degree of diversity desired in the corresponding random amino acid position.

BRIEF DESCRIPTION OF THE DRAWINGS

The present invention will be more clearly understood by referring to the following drawings, in which.

MODES OF CARRYING OUT THE INVENTION

The compounds of the invention have the formula:

as shown and described above.

W, X, Y and Z in the above formula are each independently hydrogen or a protecting group. Preferably, the protecting group is selected such that the reaction between the protecting group moiety and the atom or atoms at the position being protected is a high-yield step. Further, all of the protecting groups used should be stable to the usual reaction conditions, such as are used in condensation reactions, to further manipulate the protected compound.

While a protecting group at the 3'-position may desirably be capable of selective cleavage without detrimental effect on a protecting group in the 5'-position, it should be noted that this is not always a necessary feature of the process of the invention. Specifically, in the process of the invention, both the 3'- and the 5'-positions of the dimer intermediates are deprotected, usually simultaneously. Reliance is then preferably placed on the selectivity of the 5'- over the 3'-hydroxyl group during the step of coupling the dimer with another amidite to form the desired trimer.

W can be hydrogen or any one of a wide variety of protecting groups so long as they can be removed independently of the other protective groups (X, Y and Z). Preferably, when W is a protecting group, it is a triphenylmethyl group, such as DMT (dimethoxytrityl) or monomethoxytrityl; a carbonyl-containing group such as FMOC (9-fluorenylmethyloxycarbonyl) or levulinoyl; an acid-clearable group such as pixyl; a fluoride-cleavable alkylsilyl group such as t-BDMSi (tert-butyl dimethylsilyl), triisopropyl silyl, or trimethylsilyl; and the like. Most preferably, W is the protecting group DMT.

X also may be H or any one of a wide variety of protecting groups, so long as it can be removed without destroying the product nucleotide. Preferably, X is an alkyl group, such as methyl, ethyl, isopropyl, tert-butyl, or n-hexyl; haloalkyl such as haloethyl; cyanoalkyl such as $CH_2CH_2CN$; an aryl group such as o-chlorophenyl or methoxyphenyl; and the like. Most preferably, X is a cyanoalkyl group such as $CH_2CH_2CN$.

Y may be H or any one of a wide variety of groups. However, as a guideline to selecting useful groups, Y should preferably be a hydrocarbon. For example, useful Y groups include alkyl groups such as methyl, ethyl, isopropyl, tert-butyl, or n-hexyl. Alternatively, two Y groups, taken together, may form a heterocyclic ring with the nitrogen atom protected, such as morpholino, piperidino, pyrollidino, and the like. Most preferably, Y is an alkyl group, such as methyl or isopropyl.

Z can be any one of large number of different protecting groups and should be chosen so as to have the same characteristics as X. Suitable examples of Z as a protecting group include an alkyl group, such as methyl, ethyl, isopropyl, tert-butyl, or n-hexyl; a cyanoalkyl group such as —$CH_2CH_2CN$; an aryl group such as o-chlorophenyl, or methoxyphenyl; and the like. Preferably, Z is cyanoalkyl such as —$CH_2CH_2CN$.

In a particularly preferred embodiment, W is DMT, X and Z are each —$CH_2CH_2CN$, and Y is an isopropyl group. Methods of manipulating various protective groups with respect to DNA are known to those of ordinary skill in the art. Using similar methods to protect the 2'-hydroxy group of an RNA molecule with a protecting group is also known, e.g., see Wang et al., "Enzymatic and NMR Analysis of Oligoribonucleotides Synthesized with 2-tert-Butyldimethylsilyl Protected Cyanoethylphosphoramidite Monomers", Nucleic Acids Research, 18:11, 3347–52 (1990).

The bases $B^1$, $B^2$ and $B^3$ are each independently selected from the group consisting of protected adenine, protected guanine, protected cytosine, protected or unprotected thymine and protected or unprotected uracil. When any one or more of $B^1$, $B^2$ and $B^3$ is adenine, cytosine or guanine, it should be protected with a group such as benzoyl, isobutyryl, phenoxyacetyl, methoxyacetyl, an amidine, or the like.

In a particularly preferred embodiment, $B^1$ is selected from the group consisting of an adenine base protected with a benzoyl protecting group, a thymine base, a cytosine base protected with a benzoyl protecting group, and a guanine base protected with an isobutyryl protecting group. In another preferred embodiment, $B^2$ is selected from the group consisting of thymine and guanine and, when $B^2$ is guanine, it is protected with an isobutyryl protecting group.

In yet another preferred embodiment, $B^3$ is selected from the group consisting of protected adenine and cytosine. When $B^3$ is either adenine or cytosine, it is preferably protected with a benzoyl protecting group.

Preferred groupings of $B^1$, $B^2$ and $B^3$, with protective groups often preferred for each grouping, are shown below:

"1" in the above formula represents the residue of a ribose or deoxyribose. Ribose is the pentose $CH_2OH(CHOH)_3CHO$ that forms the sugar backbone of an RNA polynucleotide chain in its furanose form by a series of 5'-3' sugar-phosphate links. Deoxyribose has one less hydroxy group at the 2-position of the sugar ring and is the sugar that forms the backbone of a DNA chain.

The compounds of the invention can be made by:

a. treating a nucleoside comprising a base, a ribose or deoxyribose residue, and a 5'-protecting group, with a trialkyl dimethylsilyl halide to produce the corresponding 3'- and 5'-protected nucleoside;

b. removing the 5'-protecting group;

c. coupling the resulting 5'-deprotected nucleoside with a first nucleoside phosphoramidite and oxidizing to form a phosphate triester;

d. deprotecting at the 5'- and 3'-termini to give the corresponding 3',5'-dihydroxy nucleoside;

e. coupling the dihydroxy nucleoside with a second nucleoside phosphoramidite and oxidizing to produce the corresponding 3'-hydroxy trinucleotide; and f. converting this 3'-hydroxy trinucleotide to a 3'-phosphoramidite.

Step "a." of this particularly advantageous process for making the compounds of the invention comprises treating the starting nucleoside, which has a 5'-protecting group such as DMT, with a trialkylsilyl halide, such as t-butyl dimethylsilane halide, to produce a 3'-trialkylsilyl, 5'-protected nucleoside. The reaction is illustrated below:

where W and $B_1$ are as defined above. This reaction is typically carried out in the presence of $AgNO_3$ or imidazole, which acts as a catalyst, and an organic solvent, such as pyridine or tetrahydrofuran. Preferably, the reaction takes place in an inert atmosphere, such as that provided by nitrogen or argon gas. The product may be isolated from the rest of the reaction mixture by any convenient method, such as by drowning out in a non-solvent, precipitating out, extraction with an immiscible liquid, evaporation of a solvent, or some combination of these or other methods. A particularly preferred method of adding a 3'-t-butyl dimethylsilyl protecting group is provided by Ogilvie et al., *Pure and Appl. Chem.*, 59, 325–30 (1987).

In step "b.", the pre-existing 5'-protecting group can be removed selectively by any one of a number of various procedures, for example, by treatment with a mineral acid, such as HCl or $H_2SO_4$; an organic acid such as HOAc, dichloroacetic acid, trichloroacetic acid, benzenesulfonic acid; another strong acid; a metal halide such as $ZnBr_2$ or another Lewis acid; a base such as piperadine or hydrazine; and the like.

In the removing step "b.", a solvent is typically used, such as an alcohol, acetonitrile, diethyl ether, acetone, ethyl acetate, or the like. Preferably, the solvent is acetonitrile.

The 5'-deprotected product may be isolated from the rest of the reaction mixture by any convenient method, such as by drowning out in a non-solvent, precipitating out, extraction with an immiscible liquid, evaporation of a solvent, or some combination of these or other methods. Preferably, the 3-silyl-protected nucleosides are isolated by crystallization.

Step "c." of the above-described process involves coupling the 5'-deprotected nucleoside with a first nucleoside phosphoramidite, followed by oxidation of the internucleotide trivalent phosphorous to form a phosphate triester. The first nucleoside phosphoramidite has the formula:

where W, Y, Z and $B^2$ are as defined above. Such phosphoramidites are usually available commercially under the trade name "DNA Amidites." Typically, the nucleoside phosphoramidite is used in the amount of from about 1.0 to about 1.1 equivalents, most preferably about 1.1 equivalents.

After being condensed with the 5'-deprotected nucleoside described above, and after the dinucleotide phosphite triesters have been oxidized to phosphate triesters, the coupled product has the formula:

where W, X, $B^1$ and $B^2$ are as defined above.

This dimer formation reaction typically takes place in the presence of a tetrazole for the purpose of activating the phosphoramidite. The amount of tetrazole present can vary widely between about 5 to about 10 equivalents, but preferably is about 10 equivalents. Other materials that can be substituted for tetrazole include benzotriazole and p-nitrophenyl tetrazole.

The dinucleotides are then given a deblocking procedure, such as treatment with acid, to deprotect the 5'- and 3'-termini, using one of the deblocking procedures described above, either alone or in combination with each other or other procedures known to those of ordinary skill in the art. The resulting deprotected 3',5'-dihydroxy dinucleoside is typically isolated from the rest of the reaction mixture by any convenient method, such as by drowning out in a non-solvent, precipitating out, extraction with an immiscible liquid, evaporation of a solvent, or some combination of these or other methods. A preferred isolation method is by chromatography.

Further, when a silyl protecting group is present in step "d.", a silyl cleaving agent such as KF is also typically added to the reaction mixture, primarily to diminish side reactions but also to accelerate the deprotecting reaction. Other examples of such agents include tetrabutylammonium fluoride.

Next, the deprotected 3',5'-dihydroxy dimer is coupled with a second nucleoside phosphoramidite having a base $B^3$, and the trimer product is then oxidized to produce the corresponding 3'-hydroxy trinucleotide. In a preferred embodiment, step "e." comprises coupling the deprotected dimer with the second phosphoramidite to produce the corresponding 5'-W-3'-hydroxy trinucleotide and isolating the 5'-W-3'-hydroxy trinucleotide, preferably by column chromatography. The final step, "f.", comprises converting the 5'-W-3'-hydroxy trinucleotide to the corresponding 3'-phosphoramidite trinucleotide, preferably by the procedure of Sinha et al., Tett. Lett., 24, 5843–46 (1983), and isolating this by column chromatography.

The resulting 3'-phosphoramidite trinucleotides, also called codon amidites, can be coupled onto nucleoside or nucleotide-bearing solid supports with semi-manual methods. For example, a Biosearch 8750 four-column, automated DNA synthesizer running a synthesis program without the coupling step can be used for 5'-deblocking, oxidation and capping, as well as washing between steps.

Further, a mixture of from two to twenty 3'- or 5'-phosphoramidite trinucleotide codons, or their complements, can be used to assemble a panel of codons, with each codon encoding a different amino acid. Such panels are useful for making oligomers, such as synthetic DNA fragments, by sequentially coupling the individual codons in the panel to a dC nucleoside- or nucleotide-functionalized support.

Specifically, in accordance with one of the processes of the invention, an oligonucleotide can be synthesized to encode a sequence of "n" pre-determined amino acids, or its complement. Such a process comprises the steps of:

(a) coupling a first 3'-phosphoramidite trinucleotide codon, phosphoramidite monomer, or the complement to this codon or monomer, onto a nucleoside- or nucleotide-bearing solid support;

(b) sequentially condensing with an immediately preceding codon, monomer, or complement, "n" 3'-phosphoramidite trinucleotide codons or their complements, each codon or its complement corresponding to the next pre-determined amino acid in the sequence; and (c) cleaving the oligonucleotide from the solid support.

Step (b) above, directed to sequential condensation, is as described above generally for condensation reactions. Step (a), the coupling of a codon onto a solid support, and step (c), the cleavage of the resulting oligonucleotide from the support, are performed by methods known to those of ordinary skill in the art. The cleavage procedure usually removes all protecting groups simultaneously to generate biologically active material.

An oligonucleotide encoding a peptide having at least one pre-determined amino acid position and at least one random amino acid position can be prepared in accordance with the invention by a process comprising the steps of:

(a) coupling a first 3'-phosphoramidite trinucleotide codon, phosphoramidite monomer, or the complement to said codon or monomer, onto a nucleoside- or nucleotide-bearing solid support;

(b) for each pre-determined amino acid position, sequentially coupling to an immediately preceding codon, monomer, or complement, a 3'-phosphoramidite trinucleotide codon, or its complement, corresponding to the pre-determined amino acid;

(c) for each random amino acid position, coupling to an immediately preceding codon a mixture of from two to twenty 3'-phosphoramidite trinucleotide codons, at least two of the trinucleotides representing a codon to a different amino acid; and (d) cleaving said nucleotide from the solid support.

Each pre-determined codon sequentially corresponds to each pre-determined amino acid position in the desired oligonucleotide. Further, steps (b) and (c) above are preferably combined in such a way that the identity and ratio of the codons used in each said mixture represent the degree of diversity desired in the corresponding random amino acid position.

Finally, in accordance with a third embodiment of the invention, an oligonucleotide having at least one region of random amino acid positions, which may be optionally preceded or followed by "n" pre-determined flanking amino acid sequences, or their complements, the third synthetic process of the invention comprises the steps of:

(a) coupling at least one pre-existing 3'-phosphoramidite trinucleotide codon, phosphoramidite monomer, or the complement to this codon or monomer, onto a nucleoside- or nucleotide-bearing solid support;

(b) for each random amino acid position, sequentially coupling to the immediately preceding codon, monomer, or complement, a mixture of from two to twenty pre-existing 3'-phosphoramidite trinucleotide codons, each codon corresponding to a different amino acid; and (c) cleaving the oligonucleotide from the solid support.

The identity and ratio of codons used in each mixture represent the degree of diversity desired in the corresponding random amino acid position.

These processes of the invention for making oligonucleotides provide new methods for building diverse DNA libraries, using the pre-formed triplet codons in combination with reliable phosphoramidite DNA synthesis. Although coupling efficiencies may be modest, the amplification power of the polymerase chain reaction (PCR) renders them adequate for a wide range of purposes. For example, combinatorial libraries using a systematically diversified sets of monomers have been made by chemical means. Using the codon amidites of the invention, the advantages of a practical synthetic pathway and the ability to thoroughly characterize the resulting compounds can now be extended to recombinant libraries. Selected subsets of amino acids can be used to analyze structure/function relationships in a wide variety of contexts, such as the role of steric bulk versus electronic properties in a particular chemical environment. Specifically, the striking biases that exist in amino acids present at short distances from bound ligands have already been noted in a collection of about 50 protein crystal structures, thus enabling the synthesis of novel binding sites by directed mutagenesis. This, in turn, results in the ability to produce more selectively targeted biological materials such as drugs and diagnostic markers.

It is therefore seen that the compositions and processes of the invention are superior to the generation of codons using mixtures of monomers to obtain a random mix of amino acids in a particular position, because (1) stop codons are eliminated; (2) the codons expressed are more easily controlled, particularly when the expression of a library containing less than 20 amino acids at a given site is desired; and (3) the codon redundancy inherent in the standard N-N-(G/C) mixed site is eliminated since an inflated library size is not needed to achieve complete representation. Moreover, the compositions and processes of the invention are clearly superior to the physical support-splitting methods, which involve repetitive coupling, mixing, and dividing steps, since less labor is required. Further, only a modest synthesis scale is needed to provide all of the desired sequences.

The following examples are intended to illustrate but not to limit the invention.

EXAMPLE 1

Preparation of N⁴-Benzoyl-3'-tert-butyldimethylsilyl Deoxycytidine where $B^1$ is $C^{bz}$.

A solution of 5 g (7.9 mmol) N⁴-benzoyl-5'-O-(4,4'-dimethoxytrityl)-2'-deoxycytidine in 200 mL of pyridine was reduced to a foam in vacuo. Another 200 mL of pyridine and 2.5 g of AgNO₃ was added, and about 50 mL of the pyridine solvent was removed by rotary evaporation. The flask containing the reaction mixture was flushed with argon, and 3 g of the solid tert-butyldimethylsilyl chloride (TBDMS-Cl) (19.8 mmol) was added. The resulting solution was allowed to stand overnight.

The next day, 10 mL of methanol was added, and the reaction mixture was reduced to a solid in vacuo. 200 mL of ethyl acetate and 100 mL of water were added, and the mixture was transferred to a separatory funnel and allowed to separate. After separating, the organic layer was washed with 100 mL of water and dried over anhydrous Na₂SO₄. The solution was reduced to a foam and subjected to high vacuum overnight. The yield was 5.8 g (98%) of a single spot material (rf 0.81 in 9:1 CH₂Cl₂:MeOH).

This 3'-protected product was dissolved in 200 mL CH₃CN, and 10 mL of 6N HCl was added. The reaction mixture turned red, was allowed to stand for one minute, and then was neutralized to a colorless endpoint by adding 28% aqueous ammonia. The solution was reduced to a solid in vacuo. The solid was dissolved in 200 mL of methanol. When 100 mL of water were added, the solution became cloudy. The mixture was placed in a separatory funnel and washed with 200 mL of hexane. Crystals formed in the aqueous layer, and these were collected by filtration and washed with hexane. The aqueous layer was then chilled, and the resulting crystals were combined with those previously obtained to give 2.5 g of white powder (73% yield; rf 0.64; mp 105°–110° C.).

¹H NMR (300 mHz, CDCl₃): δ 8.3 (d, 1H); 7.8 (d, 2H); 7.5 (d, 2H); 7.4 (5, 3H); 7.2 (s, 1H); 6.15 (s, 1H); 4.45 (m, 1H); 3.95 (s, 2H); 3.75 (s, 2H); 2.4 (m, 1H); 2.3 (m, 1H); 0.8 (s, 9H); 0.0 (s, 6H).
m/z 469.7, calculated. MNa⁺ 469.7.

EXAMPLE 2

Preparation of Thymidine-3'-yl N⁴-Benzoyldeoxycytidine-5'-yl Cyanoethylphosphate where $B^1$ is $C^{bz}$ and $B^2$ is T.

A solution of 1 g (2.2 mmol) N⁴-benzoyl-3'-tert-butyldimethylsilyl deoxycytidine in 150 mL of dry CH₃CN was reduced to a foam in vacuo. The procedure was repeated, and the residue was subjected to high vacuum for one hour. About 40 mL of dry CH₃CN was added and, after the solid starting material dissolved, 2 g (2.7 mmol) of 5'-O-(4,4'-dimethoxytrityl)thymidine-3'-O-(2-cyanoethyl-N,N-diisopropylphosphoramidite was added. To this was added 10 mL of 0.5N tetrazole in dry CH₃CN, and the mixture was allowed to stand for 15 minutes. 150 mL of ethyl acetate, 50 mL of water, 100 μL of pyridine, and 2 g of iodine were added, and the mixture was shaken until an orange color persisted. To this was added 4 g of Na₂S₂O₃, and the mixture was shaken in a separatory funnel until the orange color disappeared. The layers were separated, and the organic phase was washed with 200 mL of a saturated solution of NaHCO₃ in water and dried over anhydrous Na₂SO₄. The solution was filtered and reduced to a foam in vacuo. The yield was 2.7 g (100%; rf 0.6 in 10% MeOH/CH₂Cl₂). H.R.M.S. calculated for C₅₆H₆₆N₆O₁₄SiP: 1105.4144. Found: 1105.4164.

This product was dissolved in 100 mL CH₃CN, and 10 mL of 6N HCl were added. The reaction mixture turned orange and was allowed to stand for 90 minutes. Cautiously, 28% aqueous ammonia was added until the orange color disappeared. 5 mL of pyridine was then added. The solution was reduced to a solid in vacuo and subjected to a high vacuum overnight. The solid was partially dissolved in 40 mL of 5% MeOH/CH₂Cl₂ and applied to a bed of silica (4×15 cm) packed with the same solvent. Elution proceeded with a series of MeOH/CH₂Cl₂ mixtures, as follows: 500 mL of 5% MeOH, 500 mL of 10%, 500 mL of 15%, and 500 mL of 20% MeOH/CH₂Cl₂. The product-containing fractions eluted at 20% MeOH/CH₂Cl₂, were pooled, and then reduced in vacuo to give, after high vacuum overnight, 1.2 g of a clear tar (68% yield; rf 0.19 at 10% MeOH/CH₂Cl₂). MALDI m/z 711.6, calculated. MNa⁺ 711.

¹H NMR (400 mHz, DMSO D₆): δ 11.2 (s, 1H); 11.1 (m, 1H); 8.1 (d, 1H); 7.9 (d, 2H); 7.6 (s, 1H); 7.5 (t, 1H); 7.4

(t, 2H); 7.2 (s, 1H); 6.1 (m, 2H); 5.4 (d, 1H); 5.1 (m, 1H); 4.9 (m, 1H); 4.1 (m, 5H); 3.9 (m, 2H); 3.5 (m, 2H); 2.8 (5, 2H); 2.3 (m, 3H); 2.0 (m, 1H).

EXAMPLE 3

Preparation of $N^6$-Benzoyl-5'-O-(4,4'-dimethoxytrityl)deoxyadenosine-3'-yl Cyanoethylphosphate-5'-yl Thymidine-3'-yl N4-Benzoyldeoxycytidine-5'-yl Cyanoethylphosphate where $B^1$ is $C^{bz}$, $B^2$ is T, and $B^3$ is $A^{bz}$.

A solution of 1.2 g (1.4 mmol) of thymidine-3'-yl $N^4$-benzoyldeoxycytidine-5'-yl cyanoethylphosphate in a mixture of 100 mL dry $CH_3CN$ and 10 mL DMSO was reduced to a volume of about 10 mL in vacuo. This process was repeated with 100 mL of dry $CH_3CN$.

After flushing with argon, 60 mL dry $CH_3CN$ and 10 ml of 0.5N tetrazole in $CH_3CN$ were added. Three aliquots of 500 mg $N^6$-benzoyl-5'-O-(4,4'-dimethoxytrityl)deoxyadenosine-3'-O-(2-cyanoethyl)-N,N-diisopropylphosphoramidite were added at 10 minute intervals (total 1.5 g, 1.7 mmol). After 10 minutes, 150 mL of ethyl acetate and 50 mL of water were added, along with 100 μL of pyridine. About 1 g of iodine was then added, and the flask was shaken until an orange color persisted. To this was added 4 g of $Na_2S_2O_3$, and the mixture was shaken until the orange color disappeared. The layers were separated, and the organic phase was washed with 200 mL of saturated $NaHCO_3$ solution and dried over anhydrous $Na_2SO_4$. The mixture was filtered, and the filtrate was reduced to a foam in vacuo. A silica column (3×12 cm) was prepared using 2% methanol and 1% pyridine in $CH_2Cl_2$. The trimer product was applied to the column using 20 mL of the same solvent. Elution proceeded with a series of $MeOH/CH_2Cl_2$ mixtures, specifically, 200 ml of 2% MeOH, 200 ml of 4%, 200 mL 6%, 200 mL 8%, 200 mL 10%, 200 mL 12%, and 200 mL of 14% $MeOH/CH_2Cl_2$. The product-bearing fractions, which eluted at 14% $MeOH/CH_2Cl_2$, were pooled and reduced in vacuo to give 600 mg (29% yield) of the desired trimer (rf 0.28 in 10% $MeOH/CH_2Cl_2$).

MALDI m/z 1492, calc'd. $MNa^+$ 1489.

$^1H$ NMR (400 mHz, $CDCl_3$): δ 8.6 (d, 1H); 8.2 (d, 1H); 8.03 (t, 1H); 8.0 (d, 2H); 7.8 (t, 2H); 7.6–7.1 (m, 17H); 6.8 (m, 4H); 6.5 (t, 1H); 6.1 (s, 1H); 6.0 (m, 1H); 5.3 (broad s, 1H); 5.2 (s, 1H); 5.0 (broad s, 1H); 4.5–4.2 (m, 15H); 3.8 (s, 6H); 3.4 (m, 2H); 3.2 (m, 1H); 2.8–2.2 (m, 12H); 1.8 (m, 3H).

EXAMPLE 4

Preparation of $N^6$-Benzoyl-5'-O-(4,4'-dimethoxytrityl)deoxyadenosine-3'-yl Cyanoethylphosphate-5'-yl Thymidine-3'-yl $N^4$-Benzoyldeoxycytidine-5'-yl Cyanoethylphosphate-3-O-(2-cyanoethyl)-N,N-diisopropylphosphoramidite where $B^1$ is $C^{bz}$, $B^2$ is T, and $B^3$ is $A^{bz}$.

A mixture of 50 mL of $CH_3CN$ and 100 ml THF were used to dissolve 400 mg (0.27 mmol) of $N^6$-benzoyl-5'-O-(4,4'-dimethoxytrityl)deoxyadenosine-3'-yl cyanoethylphosphate-5'-yl thymidine-3'-yl $N^4$-benzoyldeoxycytidine-5'-yl cyanoethylphosphate (from Example 3). The solution was stripped to a solid in vacuo. After argon was blown into the flask, the solid was re-dissolved in 60 mL THF. About 1 mL of diisopropylethylamine (DIPEA) was added, along with 300 µL 2-cyanoethyl-N,N-diisopropylchlorophosphoramidite (318 mg, 1.3 mm). The solution was allowed to stand for 20 minutes, and 5 mL of 5% aqueous $NaHCO_3$ were added. The solvent was removed in vacuo, and 100 mL of ethyl acetate was added. The solution was washed with 60 mL of a 5% aqueous solution of $NaHCO_3$, dried over $Na_2SO_4$, and reduced to a solid in vacuo. A silica column (2×7 cm) was prepared using 2% methanol and 1% pyridine in $CH_2Cl_2$. The crude product was applied to the column using 10 mL of this solvent. Elution proceeded with a series of MeOH/$CH_2Cl_2$ mixtures, specifically, 100 mL of 2% MeOH/$CH_2Cl_2$, 100 mL of 3%, 100 mL 4%, 100 mL 5% and 100 mL of 6% MeOH/$CH_2Cl_2$. The product-bearing fractions, which eluted at 6% MeOH/$CH_2Cl_2$, were pooled and reduced in vacuo to give 140 mg (31% yield) of the desired codon amidite (rf 0.45 at 10% MeOH/$CH_2Cl_2$).

$^{31}P$ NMR (162 mHz, $CDCl_3$): δ 8 147.2, 147.16, ($P^{III}$), −4.560, −5.563 ($P^V$). Area ratio $p^{III}/P^V$=20.243/39.782.

Anal. Calc'd for $C_{82}H_{97}N_{14}O_{20}P_3 \cdot CH_2Cl_2$: C, 56.24; H, 5.58; N, 11.19. Found: C, 55.91; H, 5.23; N, 11.32.

EXAMPLE 5

Preparation of Other Codon Phosphoramidite Compounds

The following additional trinucleotide codon phosphoramidites made by the general methods described above in Examples 1–4.

wherein

W is DMT, X and Z are both —$CH_2CH_2CN$, and Y is diisopropyl amine;

A is hydrogen or hydroxy; and $B^1$, $B^2$ and $B^3$ for Compounds 1–4 are as shown below:

Compound 1: $B^3=A^{bz}$; $B^2=T$; and $B^1=A^{bz}$

Compound 2: $B^3=T$; $B^2=T$; and $B^1=C^{bz}$

Compound 3: $B^3=G^{ibu}$; $B^2=T$; and $B^1=A^{bz}$

Compound 4: $B^3=C^{bz}$; $B^2=G^{ibu}$; and $B^1=A^{bz}$

EXAMPLE 6

DNA Synthesis and Analysis

The codon amidite triplets dATA, dCTT, dATC, dATG and dAGC were made by solution phase methods and converted into codon 3'-phosphoramidites, with protecting groups that are fully compatible with automated phosphoramidite DNA synthesis chemistry. The 3'-hydroxyls were converted into N,N-diisopropyl-β-cyanoethylphosphoramidites using the general method described above in Examples 1–4. The resulting codon amidites were single spot by thin layer chromatography (TLC), and two of the compounds appeared to be more than 90% pure by $^{31}P$ NMR.

These individual codon amidites were subjected to several functional tests. First, the individual codons were used to make a 16-mer dATACTTATCATGAGCC (SEQ ID NO: 2) by sequential coupling onto a nucleoside-bearing, dC-functionalized solid support, using semi-manual methods. A Biosearch 8750 four-column, automated DNA synthesizer, running a synthesis program without the coupling step, was used for detritylation, oxidation and capping, as well as washing between steps.

Coupling was done manually in the following manner. Under argon, the codon amidite was dissolved in acetonitrile to make a 100 mg/mL solution, and 100 µL of this solution was taken up in a 1-cc tuberculin syringe (luer slip-tip). Tetrazole was dissolved in $CH_3CN$ to make a 0.6M solution, of which 100 µL was taken up in a second syringe.

The DNA synthesizer instrument was paused before the time that coupling would normally occur, and the liquid was removed from the column by an argon drying step. The column was removed from the instrument, and one syringe was inserted into each end of the column. The syringe containing the amidite was discharged into the column. The excess volume was allowed to enter the syringe containing the tetrazole solution at the opposite end. Next, the tetrazole-containing syringe was discharged, and the first syringe was allowed to fill with excess mixed fluid. The process was repeated three times, and the column was allowed to stand for 1 minute.

After the syringes were removed, the column was placed back on the instrument. Oxidation, capping and detritylation steps were performed as appropriate to complete the desired DNA structure. At the end of the synthesis, the DNA fragment was cleaved from the solid support and, at the same time, the exocyclic amine and internucleotide phosphate protecting groups were removed by treating the DNA product with concentrated NH$_4$OH for 72 hours at room temperature. Oligopac reverse phase cartridges (commercially available from Millipore Corp.) and the associated protocols for these cartridges were used for purification. On a 0.2 μM synthesis scale, 2 O.D. units (260 nm) of DNA were obtained after the cartridge purification procedure.

Figure 1A:
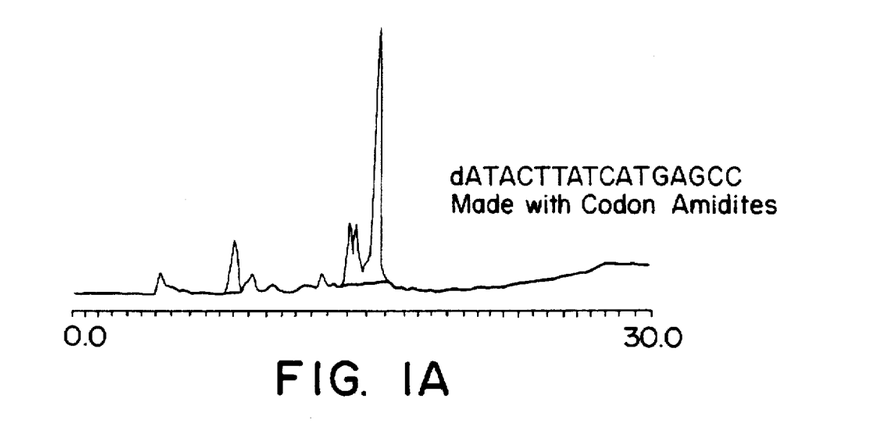
FIG. 1A shows a SAX HPLC trace of 16-mer oligonucleotide dATACTTARCATGAGCC (SEQ ID NO: 1) made with the codon amidites of the invention.
Figure 1B:
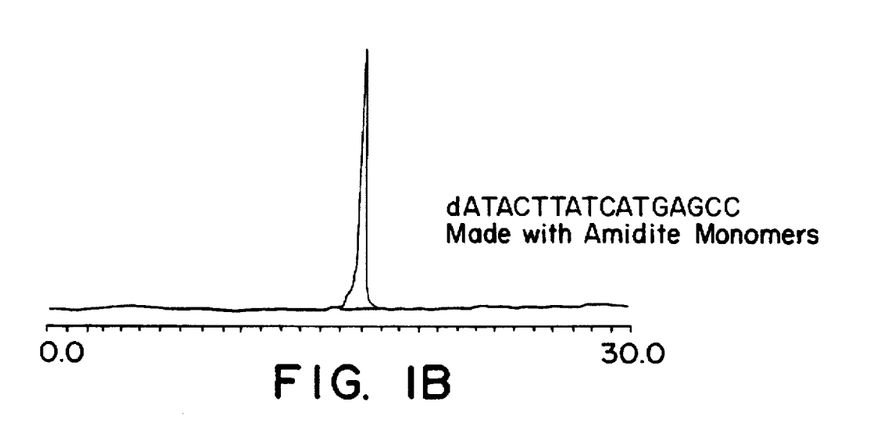
FIG. 1B shows a SAX HPLC trace of the same 16-mer oligonucleotide dATACTTARCATGAGCC (SEQ ID NO: 1) made with amidite monomers.
Figure 1C:
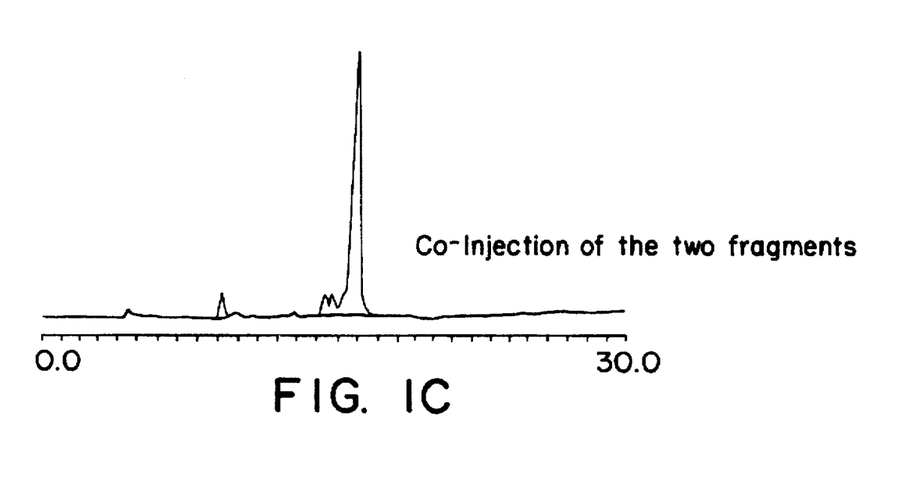
FIG. 1C shows a SAX HPLC trace of the result when both the fragment of FIG. 1A and the fragment of FIG. 1B are co-injected.
Figure 2:
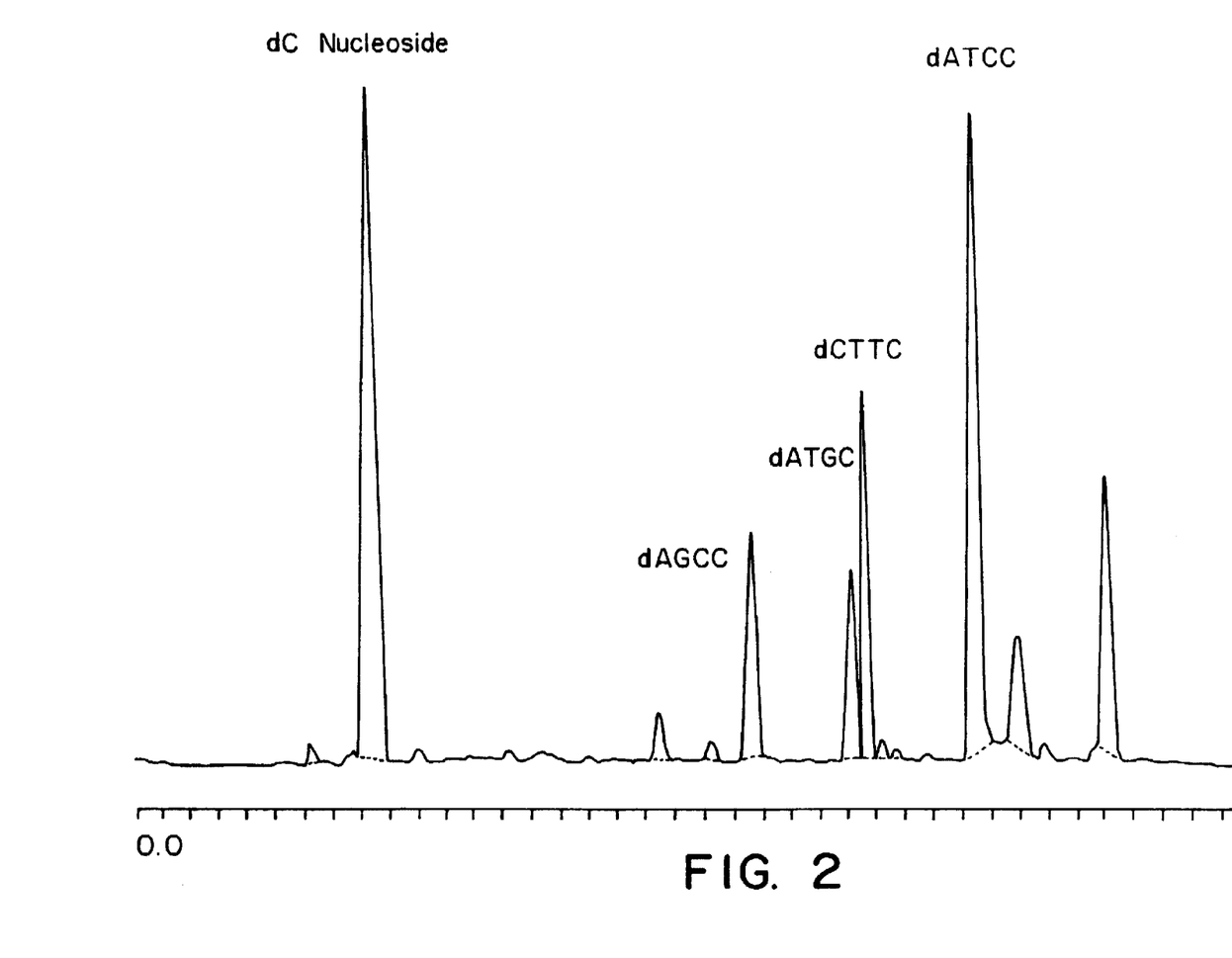
FIG. 2 shows the results of analysis by reverse phase HPLC of coupling a codon amidite mixture to dC support.

The same sequence was then made with monomers and, when tested by co-elution on SAX HPLC, the DNA fragment obtained appeared to be identical to the sequence made with monomers. See FIGS. 1A, 1B and 1C. The details of the SAX HPLC analysis are as follows: A 5×250 mm column of Whatman Partisil-10 was used. Buffer A, 0.002M phosphate in 20% CH$_3$CN at pH 6.8, and Buffer B, 0.2M phosphate in 20% CH$_3$CN at pH 6.8, were both prepared. The gradient used was 0–75% Buffer B over a 30-minute period, at a flow rate of 1.5 ml/min. The product was detected at 260 nm.

Snake venom phosphodiesterase/calf alkaline phosphatase digests of both 16-mers also looked identical, further establishing the structural integrity of the DNA fragments made by the method of the invention.

Next, to evaluate the relative coupling efficiency of the codon amidites, a roughly equimolar mixture of five different codons was coupled to a dC-functionalized solid support. Product tetramers made by coupling the codon amidites were quantified by analytical HPLC. The coupling efficiency of the codon amidite mixture averaged 71%, as compared to the 95–99% coupling efficiency observed for monomers.

The results of co-injection with tetramer standards prepared with monomers showed substantial incorporation of four out of five trimer codon amidites being tested and confirmed that the identity of each of the tetramers produced was consistent with the intended reaction.

For calculation of the relative amounts of tetramers in the HPLC trace, molar extinction coefficients for the nucleoside monomers were measured in 50% aqueous methanol at 260 nm: dA (13000); dG (11100); T (7550); dC (4700). These values were used to correct the areas used to represent the mole % of each species present: CTTC (30.2%); ATCC (46.5%); ATGC (10.0%); and AGCC (13.2%).

EXAMPLE 7

Recombinant DNA Methods

The codon amidites were then used to produce a "scrambled region", in which 15 internal base pairs were randomized by coupling a mixture of all five codons (dATA, dCTT, dATC, dATG and dAGC) at five sequential sites. These scrambled regions were flanked by homologous regions made with amidite monomers. The procedure yielded a pool of 54-mer fragments with the sequence shown below in Table 1 as "Codon Amidite 1."

TABLE 1

DNA Sequences Used

| Name | Sequence |
| --- | --- |
| GST-P1 SfiI | 5'- CATGCCATGACTCGCGGCCCAGCCGCC-CATGGCATGCCTCCATACACAGTTGTTTA- 3' (SEQ ID no:3) |
| Codon Amidite 1 | 5'- CCAGCATTCTGCGGCCGC(XXX)$_5$GGGGA-GGTTCACGTACTCAGG- 3' (SEQ ID no:4) |

The DNA was purified on a reverse phase cartridge. For the reverse phase analysis, a YMC Corp. C-18 column (5×250 mm) having a particle size of 5 μ was used. Buffer A was 5% MeOH in 0.001M TEAA, pH 7.5. Buffer B was 90% MeOH in 0.001M TEAA, pH 7.5. The gradient was 0–100% Buffer B over 30 minutes, with product being detected at 260 nm. With 0.2 μM of support-immobilized initial nucleoside, 5 O.D. units of purified 54-mer were obtained. The oligonucleotide was further purified by denaturing urea/acrylamide gel electrophoresis.

This resulting 54-mer pool was used as a primer in the PCR amplification of cDNA encoding a human glutathione S-transferase. The human glutathione S-transferase P1-1 cDNA in the expression vector pKXHP1 was used as a PCR template, in accordance with the procedure of Widersten, *Comprehensive Summaries of Uppsala Dissertations from the Faculty of Science* 383, Uppsala ISBN 91-554-9240-8 (1992). As a preliminary step, to eliminate an internal SfiI site at position 573–585 in the human P1-1 cDNA, overlap PCR mutagenesis was performed. A G-to-A substitution at position 582 removed the SfiI site, while leaving the amino acid sequence unchanged.

For randomization of amino acids corresponding to position 204–210 (INGNGKQ), the following amplification was performed with the codon amidite primer pool. The PCR reaction contained 25 pmol each of the primers GST-P1 SfiI and Codon Amidite 1 (shown above in Table 1), Perkin-Elmer Taq polymerase buffer with MgCl$_2$ added to 2 mM, 10 ng of template pKXHP1, all four dNTP's at 250 μM each, and 2.5 units of Taq polymerase, in a final volume of 50 μl.

Using an Omnigene thermal cycler, the reaction mixes were put through 25 cycles of denaturation (94° C., 1 minute); annealing (65° C., 1 minute); and extension (72° C., 1 minute); followed by a final cycle of extension (72° C., 10 minutes). The reaction product was gel purified, digested with SfiI and NotI, and gel purified once again.

The digested cDNA pool was subcloned into a phagemid vector by ligating to 20 ng SfiI/NotI-restricted pHEN-1 phagemid vector in a standard ligation reaction. Ligated phagemid DNA was then electrotransformed into TG-1 by the procedure of Hoogenboom et al., *Nuc. Acids Res.*, 19, 4133–37 (1991). After insertion of the mutagenized cDNA pool into the phagemid vector, sixteen transformants were randomly selected from this mini-library and were sequenced to evaluate the incorporation of the scrambled codon region. The recombinant clones were sequenced through the randomized region using the primer CTATGCG-GCCCCATTCA (SEQ ID NO: 5) in the dideoxy chain-termination method of Sanger et al., *Proc. Natl. Acad. Sci. USA*, 74, 5463–67 (1977).

These clones showed random incorporation of the proper codon sequences at the correct location. Table 2 below shows all of the codon sequences read in the 16 clones.

TABLE 2

| Clone | Sequence |
|---|---|
| 1 | ATC—ATG—ATG—ATC—CTT (SEQ ID NO: 6) |
| 2 | ATG—ATC—ATC—ATG—CTT (SEQ ID NO: 7) |
| 3 | AGC—AGC—ATC—CTT—ATC (SEQ ID NO: 8) |
| 4 | ATC—ATG—ATC—ATC—ATC (SEQ ID NO: 9) |
| 5 | AGC—CTT—ATC—ATC (SEQ ID NO: 10) |
| 6 | ATC—ATC—ATC—CTT (SEQ ID NO: 11) |
| 7 | ATC—CTT—ATC—ATC (SEQ ID NO: 12) |
| 8 | ATG—CTT—ATC—CTT (SEQ ID NO: 13) |
| 9 | AGC—ATC—ATC—CTT (SEQ ID NO: 14) |
| 10 | CTT—CTT—ATC—AGC (SEQ ID NO: 15) |
| 11 | AGC—ATC—ATC—ATG—CTT (SEQ ID NO: 16) |
| 12 | ATG—ATC—CTT—ATC (SEQ ID NO: 17) |
| 13 | ATC—CTT—ATC—CTT (SEQ ID NO: 18) |
| 14 | AGC—ATC—CTT—CTT—ATC (SEQ ID NO: 19) |
| 15 | ATC—ATA—ATC—ATC (SEQ ID NO: 20) |
| 16 | ATC—ATC—AGC—ATG (SEQ ID NO: 21) |

Table 3 below lists the frequency and relative amounts of each codon transcript expressed.

| Codon Amidite | Transcript Seen | Frequency | Rel. % |
|---|---|---|---|
| ATA | TAT | 1 | 1.4 |
| CTT | AAG | 17 | 24.6 |
| ATC | GAT | 34 | 43.9 |
| ATG | CAT | 9 | 13.0 |
| AGC | GCT | 8 | 11.6 |

Thus, the transcribed base sequences in the scrambled region matched those expected from the codon amidites, with reasonable correlation with the values obtained by the tetramer HPLC analysis above.

EXAMPLE 8

Altering Proportions of Amidites to Improve Representation

In this experiment, the same procedures used in Example 7 were repeated, except that the concentration of the more reactive codon amidites was lowered in an attempt to make expression of each codon more equal, based on the frequencies seen above in Example 7. Four out of 19 randomly selected clones had full length library regions. The lower expression quality was believed to be a function of lower overall codon amidite concentration. However, the results did show the desired increase in dATG and decrease in dATC, establishing that changing the relative concentration of the codon amidites in the coupling mixture has a serviceable effect on expression. Taking all of the data together, the expression ratios of codons in the clones were closely mirrored by the tetramer model coupling.

The inventors have therefore demonstrated the ability to construct desirably diversified DNA libraries using preformed triplet codon amidites and conventional phosphoramidite DNA synthesis.

We claim:

1. A process for making a compound of the formula:

wherein

W, X, Y and Z are each independently hydrogen or a protecting group, with the proviso that X is not an alkyl group;

$B^1$, $B^2$ and $B^3$ are independently a base selected from the group consisting of protected adenine, protected guanine, protected cytosine, protected or unprotected thymine and protected or unprotected uracil; and A is hydrogen or hydroxy, comprising the steps of:

a. treating a nucleoside comprising a base, a ribose or deoxyribose residue, and a 5'-protecting group, with a trialkylsilyl halide to produce the corresponding 3'- and 5'-protected nucleoside;

b. removing the 5'-protecting group to produce a 5'-deprotected nucleoside;

c. coupling the 5'-deprotected nucleoside with a first nucleoside phosphoramidite and then oxidizing to form a phosphate triester;

d. deprotecting at the 5'- and 3'-termini to give the corresponding 3',5'-dihydroxy dinucleoside;

e. coupling the dihydroxy dinucleoside with a second nucleoside phosphoramidite and oxidizing to produce the corresponding 3'-hydroxy trinucleotide; and f. converting the 3'-hydroxy trinucleotide to a 3'-phosphoramidite.

2. The process of claim 1 wherein said removing step "b." is conducted under acid conditions.

3. The process of claim 1 wherein, in said removing step "b.", acetonitrile is used as a solvent.

4. The process of claim 1 wherein, in said removing step "d.", an alcohol or acetonitrile is used as a solvent.

5. The process of claim 4 wherein said alcohol is methanol.

6. The process of claim 1 wherein, in step "d.", KF is added to the reaction mixture.

* * * * *